United States Patent [19]

Hanano et al.

[11] Patent Number: 4,699,610
[45] Date of Patent: Oct. 13, 1987

[54] CATAMENIAL TAMPON INSERTER

[75] Inventors: Yoshikazu Hanano, Isehara; Riichi Evata, Ebina, both of Japan

[73] Assignee: Lion Corporation, Tokyo, Japan

[21] Appl. No.: 795,434

[22] Filed: Nov. 6, 1985

[30] Foreign Application Priority Data

Nov. 29, 1984 [JP] Japan .......................... 59-181487[U]
Mar. 25, 1985 [JP] Japan ............................ 60-42914[U]

[51] Int. Cl.⁴ ............................................. A61F 13/20
[52] U.S. Cl. ........................................ 604/16; 604/904
[58] Field of Search ................... 604/11, 13, 14, 15, 604/16, 18, 358, 904

[56] References Cited

U.S. PATENT DOCUMENTS 3,983,868 10/1976 Ring ......................................... 604/15
3,998,225 12/1976 Hytonen ................................. 604/11
4,276,881 7/1981 Lilaonitkul ............................. 604/16
4,286,595 9/1981 Ring ....................................... 604/16
4,291,696 9/1981 Ring ....................................... 604/16

Primary Examiner—C. Fred Rosenbaum
Assistant Examiner—John D. Ferros
Attorney, Agent, or Firm—Oblon, Fisher, Spivak, McClelland & Maier

[57] ABSTRACT

An inserter for a catamenial tampon, including an outer cylinder having an ejecting hole at the fore end thereof, an ejecting inner cylinder containing a catamenial tampon therein and telescopically fitted in the outer cylinder, a projection formed on the inner surface of the side wall of the outer cylinder to transpose the tampon from the inner to the outer cylinder, and a guide groove formed axially in the side wall of the inner cylinder for engagement with the projection. The guide groove is extended to such a length that a rear end portion thereof is exposed from the outer cylinder when the inner cylinder is fully contracted thereinto.

8 Claims, 19 Drawing Figures

FIG. 7
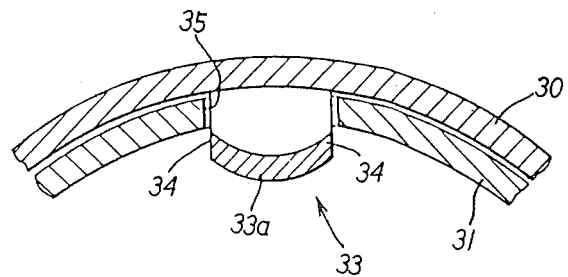
FIG. 8
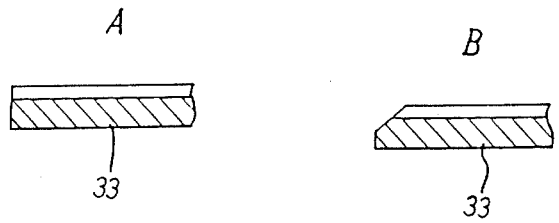
FIG. 10A          FIG. 10B
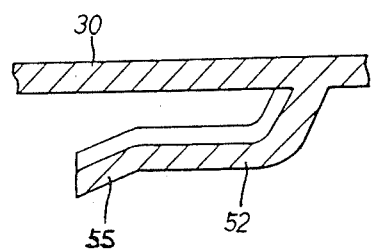    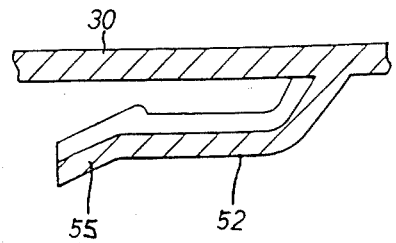

CATAMENIAL TAMPON INSERTER

BACKGROUND OF THE INVENTION

1. Field of the Invention

This invention relates to an inserter for an applicator type catamenial tampon.

2. Description of the Prior Art

As shown in FIG. 1, the known inserter for a catamenial tampon of the above-mentioned type is constituted, for example, by an outer cylinder 10 having a segmented ejecting hole 10a at the fore end thereof, and an inner cylinder 11 accommodating a catamenial tampon 12 and slidably fitted in the outer cylinder 10. The outer cylinder 10 is provided with a projection 13 on the inner surface of its side wall in engagement with a guide groove 14 formed axially in the side wall of the inner cylinder 11, thereby to push the tampon 12 into the outer cylinder 10. In use, the inner cylinder 11 is pulled out fully until the projection 13 is abutted against the fore end of the guide groove 14 as shown particularly in FIG. 2 to push the tampon 12 into the outer cylinder 10, and then the inner cylinder 11 is contracted again into the outer cylinder 10 to insert the tampon 12 into a vagina pushing open the segmented ejecting hole 10a.

If the guide groove 14 of the above-described construction is disposed downwardly during the insertion, a problem is encountered in that a withdrawal string 15 of the tampon 12 tends to droop down into the guide groove 14 as shown in FIG. 2 and be caught between the inner and outer cylinders 11 and 10 when the inner cylinder 11 is telescopically pushed into the outer cylinder 10. In this state, however, the tampon 12 is pulled out together with the inserter when the latter is removed from the vagina.

In addition, in case the strength of the projection 13 is insufficient, there arises another problem that it becomes difficult to transpose the tampon securely from the inner cylinder to the outer cylinder.

OBJECTS OF THE INVENTION

With the foregoing situations in view, the present invention has as its primary object the provision of an inserter for a catamenial tampon which can prevent the withdrawal string of the tampon from being caught between the inner and outer cylinders at the time of insertion, ensuring unobstacled ejection of the tampon.

It is another object of the present invention to provide an inserter for a catamenial tampon which is provided with a projection of a sufficient strength for pushing the tampon from the inner to the outer cylinder, thereby transposing the tampon securely into the outer cylinder prior to ejection of the tampon.

SUMMARY OF THE INVENTION

In order to achieve the above-mentioned primary object, the tampon inserter of the invention comprises: an outer cylinder having an ejecting hole at the fore end thereof; an ejecting inner cylinder slidably fitted in the outer cylinder and containing a tampon therein; a projection provided on the inner surface of the side wall of the outer cylinder for pushing the tampon into the outer cylinder; and a groove formed axially in the side wall of the inner cylinder for engagement with the projection, characterized in that the guide groove is formed in such a length that the proximal or rear end thereof is exposed from the outer cylinder when the inner cylinder is fully contracted into the outer cylinder.

With the tampon inserter of the above-described construction according to the invention, the guide groove of the inner cylinder is formed in a prolonged length so that its proximal end is exposed from the outer ccylinder when the inner cylinder is fully pushed thereinto, preventing the withdrawal string of the tampon from being caught between the inner and outer cylinders even if it droops into the guide groove prior to ejection of the tampon.

Further, according to the present invention, the projection which pushes the tampon into the outer cylinder from the inner cylinder is constituted by a plate-like body extending toward the fore end of the outer cylinder and provided with reinforcing ribs on one side thereof to guarantee a sufficient strength for transposing the tampon. Therefore, flexure or deformation of the projection which would otherwise occur at the time of pushing the tampon into the outer cylinder can be suitably prevented. Accordingly, it is possible to transpose the tampon in a secure and reliable manner.

The above and other objects, features and advantages of the invention will become apparent from the following description and the appended claims, taken in conjunction with the accompanying drawings. It is to be understood that the drawings show only preferred embodiments and should not be construed as limitative of the invention unless encompassed by the scope of the appended claims.

BRIEF DESCRIPTION OF THE DRAWINGS

In the accompanying drawings:

FIG. 7 is a schematic section taken on line VII—VII of FIG. 6.

FIGS. 8A, 8B, 9A to 9E, 10A and 10B are fragmentary sectional views showing projections of modified constructions;

DESCRIPTION OF PREFERRED EMBODIMENTS

Figure 1:
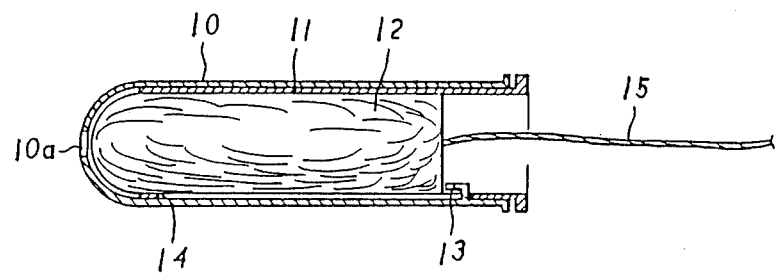
FIG. 1 is a schematic sectional view of a conventional tampon inserter.
Figure 2:
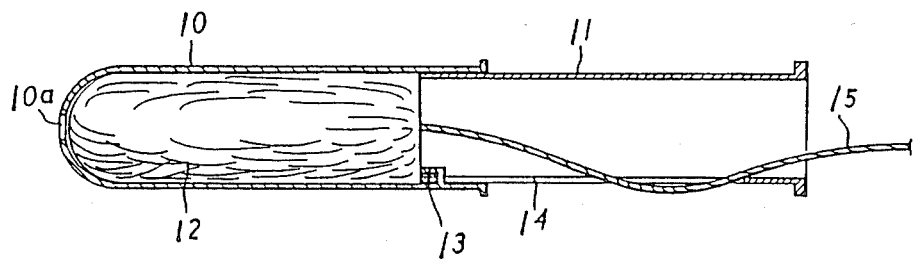
FIG. 2 is a view similar to FIG. 1 but showing the tampon in a different stage of use.
Figure 3:
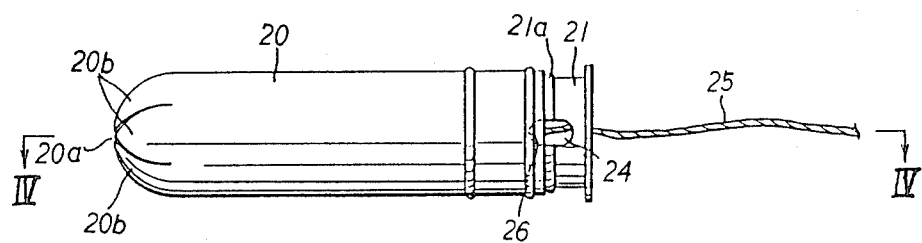
FIG. 3 is a schematic side view of a tampon inserter according to the present invention.
Figure 4:
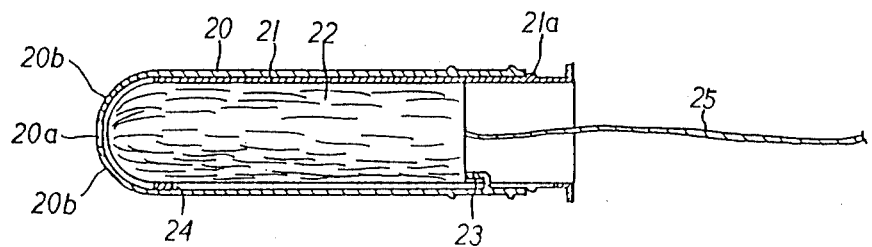
FIG. 4 is a schematic sectional view taken on line IV—IV of FIG. 3.

Hereafter, the invention is described more particularly by way of the preferred embodiments shown in the drawings. Referring to FIGS. 3 and 4, denoted at 20 is an outer cylinder formed of a synthetic resin or other flexible material, and at 21 is an inner cylinder formed of a similar material. The inner cylinder 21 which holds a tampon 22 therein is slidably fitted in the outer cylinder 20. A withdrawal string 25 is attached to the proximal end of the tampon 22.

The outer cylinder 20 is provided with an ejecting hole 20a at the fore end thereof, the ejecting hole 20a being circumvented by a plural number of converging petal-like segments 20b. These flexible segments 20b are arcuately curved and converged toward the center of the outer cylinder 20 to cover the ejecting hole 20a in a substantially closed state. The outer cylinder 20 is further provided with a projection 23 on the inner surface of its side wall at a position proximal to its rear end for pushing the tampon 22 into the outer cylinder 20 from the inner cylinder 21.

Further, the inner cylinder 21, which serves also as an ejector for extruding the tampon 22 from the outer cylinder 20 into the vagina, is provided with an elongated guide groove 24 in the axial direction to receive therein the projection 23 slidably along the length thereof. On a rear circumferential surface, the inner cylinder 21 is provided with a stopper 21a which delimits the inward telescopic movement of the inner cylinder 21 by abutting engagement with the rear end of the outer cylinder 20. The stopper 21a is provided in a position slightly inward of the rear end of the guide groove 24, so that the rear end portion of the guide groove 24 is exposed from the rear end of the outer cylinder 20 when the inner cylinder 21 is fully pushed thereinto. Further, it is also possible to make said flexible segments 20b serve as a stopper without particularly providing such stopper 21a at said position, since when the inner cylinder 21 is fully pushed into the outer cylinder 20, the inner cylinder 21 is stopped at the fully contracted state thereof by being pushed back by the reaction force of the petal-like segments 20b located at the fore end of the outer cylinder 20. In these instances, the rear end portion of the guide groove 24 needs to be exposed over a length which is sufficient for the widthdrawal string 25 of the tampon 22 to pass freely therethrough.

Figure 5:
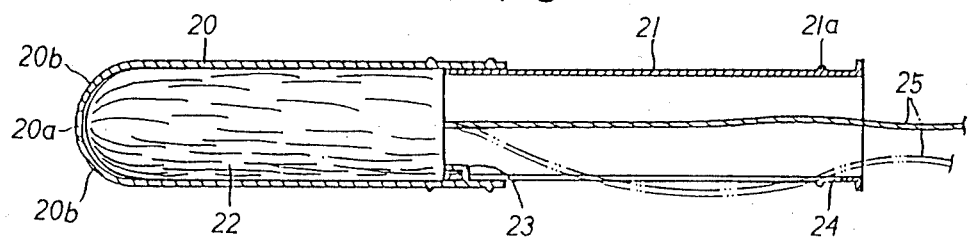
FIG. 5 is a view similar to FIG. 4 but showing the tampon in a telescopically extended state for use.

In order to use the tampon inserter, the inner cylinder 21 is fully extended out until the projection 23 is abutted against the fore end of the guide groove 24, whereupon, as shown particularly in FIG. 5, the distal end of the projection 23 is pressed against the rear end of the tampon 22, pushing the tampon 22 forward relative to the inner cylinder 21 to transpose it into the outer cylinder 20.

Succeedingly, the inner cylinder 21 is pushed into the outer cylinder 20, whereupon the rear end of the tampon 22 is pressed forward by the fore end of the inner cylinder 21 and the segments 20b of the ejecting hole 20a are pushed open by the tampon 22 to eject the tampon 22 therethrough. In this instance, even if the withdrawal string 25 of the tampon 22 droops into the guide groove 24 of the inner cylinder 21 which is telescopically extended out from the outer cylinder 20 as shown in FIG. 5 by chain line, there is no possibility of the string 25 being caught between the inner and outer cylinders 21 and 20 when the former is pushed into the latter in that state since the rear end portion of the guide groove 24 is exposed from the outer cylinder 20 in the fully contracted state (FIGS. 3 and 4) in which the stopper 21a on the inner cylinder 21 is abutted against the rear end of the outer cylinder 20. Therefore, there is no possibility of the tampon 22 being pulled out together with the inserter which is removed from a vagina after ejection of the tampon 22. In this case, the trapping of the withdrawal string 25 between the inner and outer cylinders 21 and 20 can be prevented more effectively by forming the rear end portion of the guide groove 24 arcuately as shown in FIG. 3. Further, it is recommended to provide an arcuate notch 26 at the rear end of the outer cylinder 20 in overlapping relation with the rear end portion of the guide groove 24 as indicated in phantom in FIG. 3 to enhance the above-mentioned effect all the more.

Figure 6:
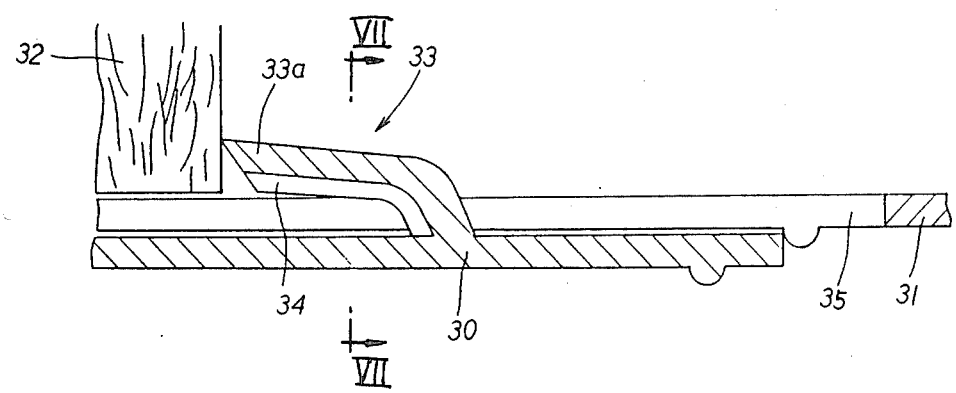
FIG. 6 is a fragmentary sectional view on an enlarged scale of major component parts in another embodiment of the invention.

FIGS. 6 and 7 illustrate another embodiment of the invention, in which the projection for transposing the tampon from the inner to the outer cylinder is shaped in a particular form. More specifically, this embodiment comprises a projection 33 shaped so that it can deform and restore its shape relatively easily when a tampon is loaded into the inner cylinder through the open rear end thereof, while ensuring a sufficient resistive force when pushing the tampon out of the inner cylinder. Namely, it is constituted by an arcuately curved plate-like projection body 33a having a thickness equivalent to or smaller than that of the outer cylinder 30, and reinforcing protuberances 34 provided along the opposite lateral sides of the projection body 33a and projected in a direction away from the axis of the outer cylinder 30. The fore end of the projection 33 is inclined toward the axis of the outer cylinder 30. Although it is preferred to cut the fore end of the projection 33 diagonally as shown in FIG. 6 so that it can firmly grip the rear end face of the tampon 32 when the latter is pushed into the outer cylinder 30, as will be described hereinlater, there may be employed a different cut, for example, a straight cut at right angles with the axis of the outer cylinder 30 as shown in FIG. 8A or a partially diagonal cut as shown in FIG. 8B.

In order to pack a tampon 32 in the inner cylinder 31 of the tampon inserter with the above-described projection 33, it is pushed into the inner cylinder 31, which is telescopically contracted in the outer cylinder 30, through the open rear end of the inner cylinder. At this time, the projection 33 is pressed and deformed outward by the tampon 32 relatively easily since the deformation takes place toward the concave side of the projection 33. Accordingly, the tampon 32 can be smoothly pushed into the inner cylinder 31. After packing the tampon 32, the projection 33 immediately resumes the original state by its increased resilient righting movement due to provision of the protuberances 34.

In order to insert a tampon 32 into a vagina by the use of the above-described tampon inserter of the invention, the inner cylinder 31 is fully pulled out until the projection 33 is abutted against the fore end of the guide groove 35 to transpose the tampon 32 into the outer cylinder 30 by pushing the tampon 32 relatively forward with the fore end of the projection 33 which is abutted against the rear end of the tampon 32. At this time, although a backward force is exerted on the projection 33 by the tampon 32 which is being pushed forward, the projection 33 which is reinforced by the protuberances 34 can transpose the tampon 32 securely without being deformed by the backward force. Succeedingly, the inner cylinder 31 is telescopically contracted again into the outer cylinder 30, whereupon the tampon 32 which is in abutting engagement at its rear end with the fore end of the inner cylinder 31 is pushed forward and ejected into the vagina through the ejecting hole 30a (not shown) of the outer cylinder 30.

Even in a case where a tampon 32 is packed into the inner cylinder 31 through its open fore end, the projection 33 which is reinforced by the protuberances 34 is unsusceptible to deformation in the backward direction when the tampon is pressed against the fore end of the projection 33, permitting the user to place the tampon 32 in the inner cylinder in a position determined by the projection 33.

The projection 33 on the outer cylinder 30 may be formed in a shape other than the one shown in FIGS. 6 and 7. In this connection, FIGS. 9A to 9E show some preferred sectional shapes of the projection.

Figure 9:
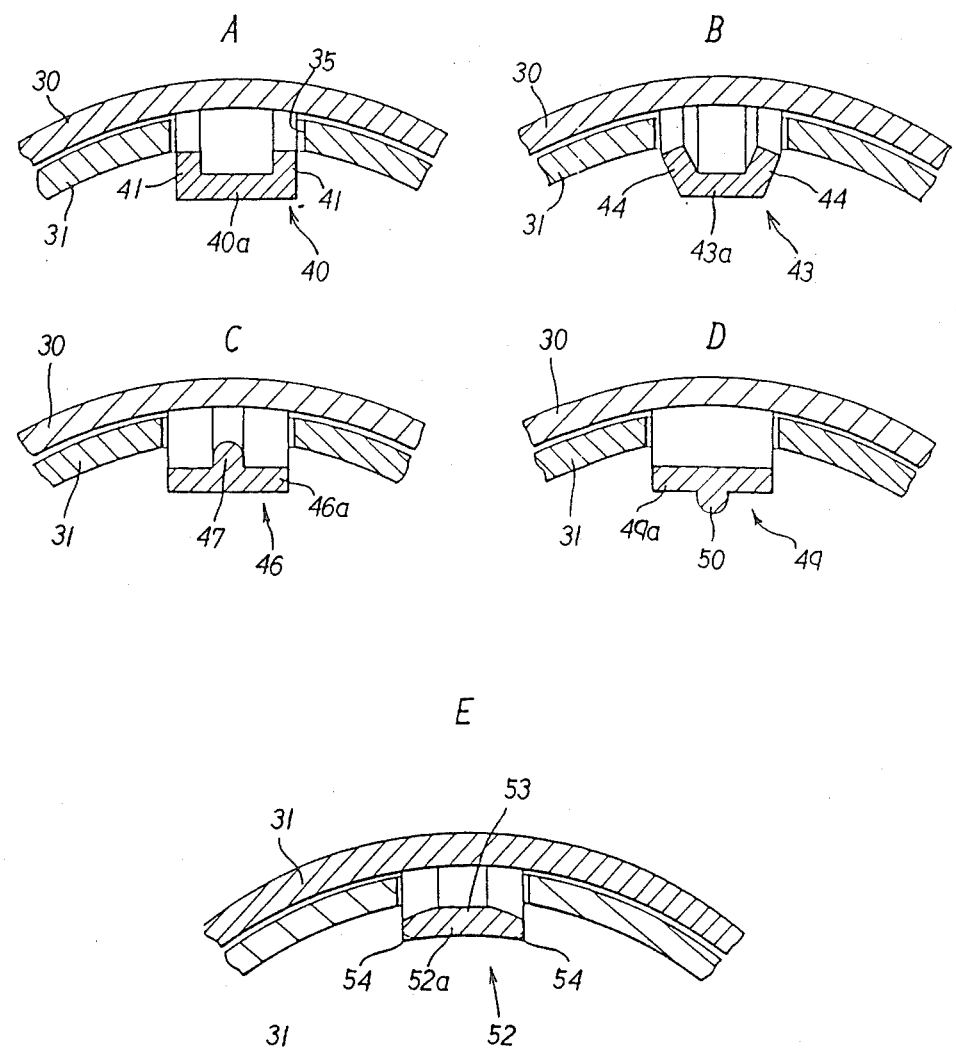

Illustrated in FIG. 9A is an example having a channel-like projection 40 with reinforcing protuberances 41 formed along its opposite lateral sides and projected in a direction away from the axis of the outer cylinder 30. In the case of FIG. 9B, protuberances 44 at the opposite sides of a main body 43a of a projection 43 diverge from each other in a direction away from the axis of the outer cylinder 30. In the examples of FIGS. 9C and 9D, flat plate-like main bodies 46a and 49a of projections 46 and 49 are provided with a single protuberance 47 or 50 on one side thereof. In FIG. 9E, the main body 52a of a projection 52 is curved in an inversed direction as compared with the projection of FIG. 7, and its thickness is increased in a center portion to form a reinforcing protuberance 53 projecting in a direction away from the axis of the outer cylinder 30. In this case, the side edges 54 of the main body 52a on the side of the axis of the outer cylinder 30 may be rounded off as indicated by chain line.

If desired, the projection 33 may be provided in parallel relation with the axis of the outer cylinder 30, or may be bent in a middle portion with its abutting fore end 55 inclined toward the axis of the outer cylinder 30 as shown in FIGS. 10A and 10B.

Further, in the foregoing embodiments, there may be employed an outer cylinder 30 with a pair of projections in radially opposing positions, in combination with an inner cylinder 31 with a pair of guide grooves.

Thus, the projection of the above-described tampon inserter of the invention is provided with a reinforcing protuberance on one side of a plate-like body which is extended forward of the outer cylinder, so that it can be deformed relatively easily in the direction of the outer cylinder by application of a pressing force, permitting the used to pack a tampon into the inner cylinder easily through the open rear end thereof. Besides, the strength of the projection can be enhanced by increasing its thickness to guarantee a higher righting strength after packing a tampon in the inner cylinder and engaging the projection securely with the rear end of the tampon. Further, the enhancement of the projection strength prevents its warping or deformation to augment its push-out function when pushing a tampon from the inner to the outer cylinder.

Figure 11:
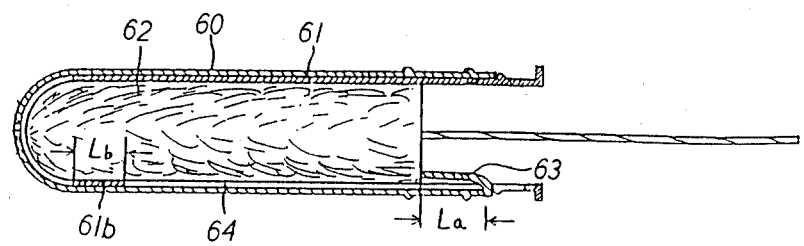
FIG. 11 is a schematic sectional view of another embodiment with a projection provided at a different position.
Figure 12:
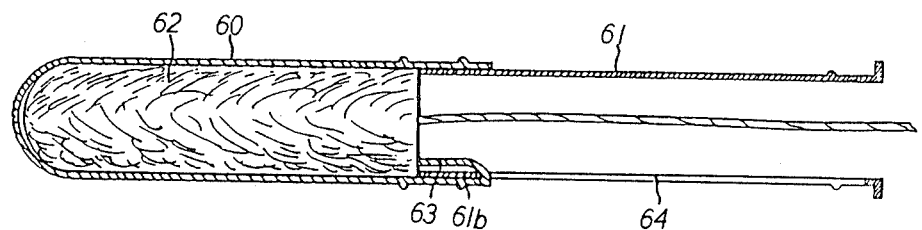
FIG. 12 is a view similar to FIG. 11 but showing the inserter in a telescopically extended state for use.

Illustrated in FIGS. 11 and 12 is a further embodiment of the invention, which is fundamentally the same as the above-described tampon inserters except in the following aspects. Namely, a projection 63 which pushes a tampon 62 for transposing the tampon 62 from an inner cylinder 61 to an outer cylinder 60 is extended axially in the direction of pushing the tampon 62 from a rear end portion of the outer cylinder 60 over a distance La which is at least 0.3 times greater than the inside diameter of the outer cylinder 60. On the other hand, a guide groove 64 is formed axially in the inner cylinder 61 such that the length Lb of a non-grooved portion 61b between the fore ends of the inner cylinder 61 and the guide groove 64 is slightly smaller than the axial length La of the projection 63. This arrangement not only prevents the withdrawal string of the tampon from being caught between the inner and outer cylinders of the inserter, but also contributes to providing an inserter which is improved in handiness and free of torsion, deformation or fracture of the inner cylinder, due to the existence of the non-grooved portion 61b of a larger length than in conventional inserters. Moreover, since the projection 63 is provided in a rear end portion of the outer cylinder 60, it becomes possible to increase the length of the projection 63 without minimizing the size of the tampon 62, as compared with the conventional counterparts, and to enhance the strength and rigidity of the inner cylinder 61 without increasing the length of the tampon inserter as a whole. The problem of strength which arises from the increase of the length of the projection 63 can be solved by employing a projecton 63 of a special shape, thereby imparting a sufficient strength for pushing the tampon into the inner cylinder securely.

Figure 13:
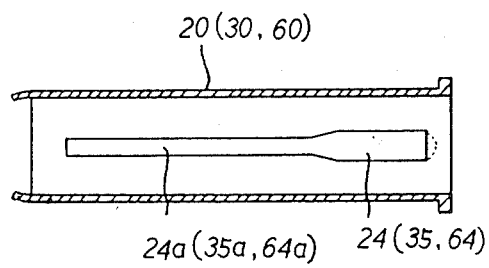
FIG. 13 is a schematic sectional view of an inner cylinder with a guide groove of a modified shape.

In the foregoing embodiments, the guide groove 24, 35 or 64 may be shaped as shown in FIG. 13, reducing the width of the groove in its major portion 24a, 35a or 64a which is located on the front side as seen in the pushing direction. This groove arrangement facilitates the engagement of the inner and outer cylinders, and prevents their unstable staggering movements. It is also possible to provide a plural number of projections and a corresponding number of guide grooves on the outer and inner cylinders, respectively.

What is claimed is:

1. A catamenial tampon assembly comprising:
   (a) an outer cylinder having a distal end that is closed except when a tampon is ejected from the distal end, an open proximal end, and an inwardly projecting projection on its inner surface adjacent its proximal end, said projection comprising:
      (i) a plate-like main body which has an outer surface, said plate-like main body being attached to said outer cylinder at its proximal end and projecting as a free cantelever toward the distal end of said outer cylinder, and
      (ii) at least one reinforcing protuberance provided on the outer surface of said plate-like main body, extending axially of said plate-like main body, and projecting in a direction away from the axis of said outer cylinder;
   (b) an inner cylinder telescopically received in said outer cylinder, said inner cylinder having an open distal end, an open proximal end for loading a catamenial tampon, and an axially extending guide groove extending therethrough, said axially extending guide groove being sized, shaped, and positioned to pass said inwardly projecting projection on the inner surface of said outer cylinder, said inner cylinder and said axially extending guide groove being sized and shaped so that, when said inner cylinder is telescoped within said outer cylinder to its maximum extent, said axially extending guide groove extends proximally of said outer cylinder, the proximal end of said axially extending guide groove being enlarged circumferentially relative to the width of the remainder of said axially extending guide groove and being arcuately shaped;
   (c) a catamenial tampon slideably received in said inner cylinder; and
   (d) a withdrawal string attached to said catamenial tampon and projecting out the proximal ends of said inner and outer cylinders.

2. A catamenial tampon assembly as recited in claim 1 wherein said outer cylinder is provided with an arcuate notch at its proximal end, said outer cylinder and said arcuate notch being sized, shaped, and positioned so that, when said inner cylinder is telescoped within said outer cylinder to its maximum extent, said arcuate notch overlaps the arcuately shaped proximal end of said axially extending guide groove.

3. A catamenial tampon assembly as recited in claim 1 wherein said plate-like main body is convex relative to the axis of said inner and outer cylinders.

4. A catamenial tampon assembly as recited in claim 1 wherein the distal end of said plate-like main body is cut obliquely to grip firmly the proximal end face of said catamenial tampon during ejection of said catamenial tampon.

5. A catamenial tampon assembly as recited in claim 1 wherein the distal end of said plate-like main body is bent inwardly toward the axis of said inner and outer cylinders.

6. A catamenial tampon assembly as recited in claim 1 wherein said at least two reinforcing protuberances extend axially of plate-like main body.

7. A catamenial tampon assembly as recited in claim 1 wherein said at least one reinforcing protuberance is formed on the radially inner surface of said plate-like main body.

8. A catamenial tampon assembly as recited in claim 1 wherein said at least one reinforcing protuberance is formed on the radially outer surface of said plate-like main body.

* * * * *